US008293318B1

(12) United States Patent
Hsu et al.

(10) Patent No.: US 8,293,318 B1
(45) Date of Patent: Oct. 23, 2012

(54) METHODS FOR MODULATING THE RELEASE RATE OF A DRUG-COATED STENT

(75) Inventors: Shaw Ling Hsu, Sunderland, MA (US); Ni Ding, San Jose, CA (US); Yiwen Tang, San Jose, CA (US); Fuh-Wei Tang, Temecula, CA (US); Lothar Walter Kleiner, Los Altos, CA (US); Syed Faiyaz Ahmed Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1339 days.

(21) Appl. No.: 11/847,222

(22) Filed: Aug. 29, 2007

Related U.S. Application Data

(60) Provisional application No. 60/841,112, filed on Aug. 29, 2006.

(51) Int. Cl.
*B05D 3/02* (2006.01)
*A61L 33/00* (2006.01)
*A61F 2/06* (2006.01)

(52) U.S. Cl. .... 427/2.24; 427/2.1; 427/2.25; 427/372.2; 427/331; 427/402; 623/1.42; 623/1.44; 623/1.46; 424/422

(58) Field of Classification Search ........... 427/2.1, 427/2.24, 372.2, 331, 402; 623/1.42, 1.44, 623/1.46; 424/422–424
See application file for complete search history.

(56) References Cited

U.S. PATENT DOCUMENTS

| | | | |
|---|---|---|---|
| 4,095,020 A | 6/1978 | Prest, Jr. et al. | |
| 4,393,093 A | 7/1983 | Sprout, Jr. | |
| 4,814,184 A * | 3/1989 | Aguadisch et al. | 424/486 |
| 4,916,193 A | 4/1990 | Tang et al. | |
| 5,385,776 A | 1/1995 | Maxfield et al. | |
| 6,096,726 A * | 8/2000 | Opolski | 514/53 |
| 6,153,252 A * | 11/2000 | Hossainy et al. | 427/2.3 |
| 6,368,658 B1 * | 4/2002 | Schwarz et al. | 427/2.15 |
| 6,413,272 B1 | 7/2002 | Igaki | |
| 6,524,274 B1 * | 2/2003 | Rosenthal et al. | 604/96.01 |
| 6,780,424 B2 | 8/2004 | Claude | |
| 6,896,965 B1 | 5/2005 | Hossainy | |
| 6,908,624 B2 | 6/2005 | Hossainy et al. | |
| 6,919,100 B2 * | 7/2005 | Narayanan | 427/2.24 |
| 6,991,759 B2 | 1/2006 | Subramaniam | |
| 7,087,263 B2 | 8/2006 | Hossainy et al. | |
| 7,094,256 B1 | 8/2006 | Shah et al. | |
| 7,166,680 B2 | 1/2007 | DesNoyer et al. | |
| 7,202,325 B2 | 4/2007 | Hossainy et al. | |
| 7,214,759 B2 | 5/2007 | Pacetti et al. | |
| 7,232,573 B1 | 6/2007 | Ding | |
| 7,244,443 B2 | 7/2007 | Pacetti | |
| 7,247,313 B2 | 7/2007 | Roorda et al. | |
| 7,261,946 B2 | 8/2007 | Claude | |
| 7,279,174 B2 | 10/2007 | Pacetti et al. | |
| 7,285,304 B1 | 10/2007 | Hossainy et al. | |
| 7,294,329 B1 | 11/2007 | Ding | |
| 7,318,932 B2 | 1/2008 | Pacetti | |
| 7,390,497 B2 | 6/2008 | DesNoyer et al. | |
| 7,419,504 B2 | 9/2008 | Hossainy | |
| 7,431,959 B1 | 10/2008 | Dehnad | |
| 7,438,722 B1 | 10/2008 | Hossainy | |
| 7,491,233 B1 | 2/2009 | Ding et al. | |
| 7,494,665 B1 | 2/2009 | Ding et al. | |
| 7,560,492 B1 | 7/2009 | Claude et al. | |
| 7,563,780 B1 | 7/2009 | Hossainy et al. | |
| 7,637,941 B1 | 12/2009 | Manicka | |
| 7,682,647 B2 | 3/2010 | Hossainy et al. | |
| 7,910,152 B2 | 3/2011 | Kleiner et al. | |
| 8,048,442 B1 | 11/2011 | Hossainy et al. | |
| 2003/0203000 A1 * | 10/2003 | Schwarz et al. | 424/423 |
| 2004/0185081 A1 | 9/2004 | Verlee et al. | |
| 2005/0112172 A1 | 5/2005 | Pacetti | |
| 2005/0208093 A1 | 9/2005 | Glauser et al. | |
| 2005/0244363 A1 | 11/2005 | Michal et al. | |
| 2005/0245637 A1 | 11/2005 | Tang et al. | |
| 2005/0265960 A1 | 12/2005 | Pacetti et al. | |
| 2005/0266038 A1 | 12/2005 | Glauser et al. | |
| 2005/0271700 A1 | 12/2005 | DesNoyer et al. | |
| 2005/0283229 A1 | 12/2005 | Dugan et al. | |
| 2005/0287184 A1 | 12/2005 | Hossainy et al. | |
| 2006/0002977 A1 | 1/2006 | Dugan | |
| 2006/0034888 A1 | 2/2006 | Pacetti et al. | |
| 2006/0067908 A1 | 3/2006 | Ding | |
| 2006/0089485 A1 | 4/2006 | Desnoyer et al. | |
| 2006/0115513 A1 | 6/2006 | Hossainy et al. | |
| 2006/0134165 A1 | 6/2006 | Pacetti | |
| 2006/0136048 A1 | 6/2006 | Pacetti et al. | |
| 2006/0182777 A1 * | 8/2006 | Kangas | 424/422 |
| 2006/0240065 A1 | 10/2006 | Chen | |
| 2006/0246108 A1 | 11/2006 | Pacetti et al. | |

(Continued)

FOREIGN PATENT DOCUMENTS

WO  WO 2007/146049  12/2007
WO  WO 2009/058666  5/2009

OTHER PUBLICATIONS

U.S. Appl. No. 09/956,521, filed Sep. 9, 2001, Hossainy et al.
U.S. Appl. No. 10/316,739, filed Dec. 10, 2002, Zhang et al.
U.S. Appl. No. 10/376,348, filed Feb. 26, 2003, Ding et al.
U.S. Appl. No. 10/807,546, filed Mar. 22, 2004, Hossainy et al.
U.S. Appl. No. 10/816,072, filed Mar 31, 2004, Dugan et al.
U.S. Appl. No. 11/187,467, filed Jul. 22, 2005, DesNoyer et al.
U.S. Appl. No. 11/437,075, filed May 18, 2006, Trollsas et al.
International Search Report for PCT/US2009/042749, mailed Aug. 5, 2010, 3 pgs.
Cheung et al., "Covered metal stent for tumor obstruction of efferent loop recurrences after gastrectomy", Ayef Wbsiaw 11, pp. 936-938 (1997).
Martin et al., "Enhancing the biological activity of immobilized osteopontin using a type-1 collagen affinity coating", J. of Biomedical Mat. Res. vol. 70, issue 1, pp. 10-19 (2004).
Spagnuolo et al., "Gas 1 is induced by VE-cadherin and vascular endothelial growth factor and inhibits endothelial cell apoptosis", Blood 103, pp. 3005-3012 (2003).
Völkel et al., "Targeting of immunoliposomes to endothelial cells using a single-chain Fv fragment directed against human endoglin (CD105)", Biochimica et Biophysica Acta 1663 pp. 158-166 (2004).

*Primary Examiner* — Timothy Meeks
*Assistant Examiner* — Cachet Sellman
(74) *Attorney, Agent, or Firm* — Squire Sanders (US) LLP

(57) ABSTRACT

Methods for modulating the release rate of a drug coated stent are disclosed.

9 Claims, No Drawings

U.S. PATENT DOCUMENTS

| | | |
|---|---|---|
| 2006/0246109 A1 | 11/2006 | Hossainy et al. |
| 2006/0251721 A1 | 11/2006 | Cruz et al. |
| 2007/0003589 A1 | 1/2007 | Astafieva et al. |
| 2007/0005130 A1 | 1/2007 | Glauser et al. |
| 2007/0009565 A1 | 1/2007 | Pacetti et al. |
| 2007/0026041 A1 | 2/2007 | DesNoyer et al. |
| 2007/0032853 A1 | 2/2007 | Hossainy et al. |
| 2007/0128246 A1 | 6/2007 | Hossainy et al. |
| 2007/0135909 A1 | 6/2007 | DesNoyer |
| 2007/0148251 A1 | 6/2007 | Hossainy et al. |
| 2007/0202147 A1 | 8/2007 | Kleiner et al. |
| 2007/0202323 A1 | 8/2007 | Kleiner et al. |
| 2007/0207181 A1 | 9/2007 | Kleiner |
| 2007/0231363 A1 | 10/2007 | Chen et al. |
| 2007/0254107 A1* | 11/2007 | Rao et al. ............ 427/372.2 |
| 2007/0259101 A1 | 11/2007 | Hossainy et al. |
| 2007/0280988 A1 | 12/2007 | Ludwig et al. |
| 2007/0286882 A1 | 12/2007 | Tang et al. |
| 2007/0286885 A1 | 12/2007 | Hossainy et al. |
| 2007/0292495 A1 | 12/2007 | Ludwig et al. |
| 2007/0292518 A1 | 12/2007 | Ludwig |
| 2007/0293941 A1 | 12/2007 | Gale et al. |
| 2007/0298257 A1 | 12/2007 | Ludwig et al. |
| 2008/0003253 A1 | 1/2008 | Glauser |
| 2008/0008736 A1 | 1/2008 | Glauser |
| 2008/0095918 A1 | 4/2008 | Kleiner et al. |
| 2008/0124372 A1 | 5/2008 | Hossainy et al. |
| 2008/0160061 A1 | 7/2008 | Hossainy et al. |
| 2008/0305141 A1 | 12/2008 | Hossainy et al. |
| 2009/0053392 A1 | 2/2009 | Kramer-Brown et al. |
| 2009/0110713 A1 | 4/2009 | Lim et al. |
| 2009/0111787 A1 | 4/2009 | Lim et al. |
| 2009/0291111 A1 | 11/2009 | Lim et al. |
| 2009/0326645 A1 | 12/2009 | Pacetti et al. |
| 2011/0086162 A1 | 4/2011 | Hossainy et al. |
| 2011/0144741 A1 | 6/2011 | Kleiner et al. |
| 2011/0151104 A1 | 6/2011 | Kleiner et al. |
| 2011/0153004 A1 | 6/2011 | Kleiner et al. |
| 2011/0200660 A1 | 8/2011 | Kleiner et al. |

* cited by examiner

METHODS FOR MODULATING THE RELEASE RATE OF A DRUG-COATED STENT

RELATED APPLICATION

This application claims benefit of and incorporates by reference as if fully set forth herein U.S. Provisional Patent Application No. 60/841,112 which was filed on Aug. 29, 2006.

FIELD OF THE INVENTION

The present invention is directed to methods for modulating the release rate of a drug coated stent.

BACKGROUND OF THE INVENTION

The traditional method of administering therapeutic agents to treat diseases of the internal organs and vasculature has been by systemic delivery. Systemic delivery involves administering a therapeutic agent at a discrete location followed by the agent migrating throughout the patient's body including, of course, to the afflicted organ or area of the vasculature.

At the other end of the spectrum is local delivery, which comprises administering the therapeutic agent directly to the afflicted site. Localized delivery of therapeutic agents may be accomplished using implantable medical devices, e.g., drug-eluting stents (DESs). The efficacy of DESs is related to their ability to release drugs in a controlled manner.

One way this is accomplished is to include on the DES a rate-controlling layer, e.g., a topcoat layer, that is disposed over a drug reservoir layer and which comprises one or more polymers selected for their ability to mediate release of a particular drug or drugs from the underlying reservoir layer. These designs often provide slow release stents since drug release rate is impeded by the presence of the topcoat layer.

Another way to control drug release from a stent is by putting drugs in a drug reservoir layer that includes a polymeric matrix that mediates the release rate of the drug. Indeed, by manipulating the drug-to-polymer ratio, drug release can be controlled.

What is needed, however, are more tunable and accurate means for providing controlled drug release from a drug reservoir layer. The current invention provides such methods and addresses other deficiencies in the art.

SUMMARY OF THE INVENTION

The present invention relates to a method that involves providing a device body, disposing a reservoir layer composition that includes a bioactive agent, a hydrophobic polymer that, if the bioactive agent is also hydrophobic, is more hydrophobic than the bioactive agent and a first hydrophobic solvent over the device body and removing the solvent from the composition to a reservoir layer. Disposing the reservoir layer composition over the device body and removing the first hydrophobic solvent from the composition are repeated until a desired reservoir layer thickness and bioactive agent concentration is achieved then a release rate curve for the bioactive agent from the reservoir layer is determined.

If a slower release rate is desired, a second hydrophobic solvent that is more hydrophobic than the first hydrophobic solvent can be substituted.

If a faster release rate is desired, a second hydrophobic solvent that is less hydrophobic than the first hydrophobic solvent can be substituted.

In various aspects, removing the solvent involves allowing the solvent to evaporate at ambient temperature or below. In this aspect, the solvent can be removed in a closed system that initially contains a partial pressure of the solvent in the system. The solvent can also be removed in a closed system that initially contains no partial pressure of the solvent in the system or can be removed in an open system.

In various aspects, removing the solvent involves heating the reservoir layer composition to a temperature above ambient temperature. In this aspect, the solvent can be removed in a closed system that initially contains a partial pressure of the solvent in the system. The solvent can also be removed in a closed system that initially contains no partial pressure of the solvent in the system or the solvent can be removed in an open system.

Another aspect of the present invention relates to a method that involves providing a device body, disposing a reservoir layer composition that includes a bioactive agent, a hydrophilic polymer that, if the bioactive agent is also hydrophilic, is more hydrophilic than the bioactive agent and a first polar solvent over the device body and removing the solvent from the composition to form a reservoir layer. Disposing a reservoir composition layer over the device body and removing the first-polar solvent from the composition are repeated until a desired reservoir layer thickness and bioactive agent concentration is achieved then a release rate curve for the bioactive agent from the reservoir layer is determined.

If a slower release rate is desired, a second polar solvent that is more polar than the first polar solvent can be substituted.

If a faster release rate is desired, a second polar solvent that is less polar than the first polar solvent can be substituted.

In various aspects, removing the solvent involves allowing the solvent to evaporate at ambient temperature or below. In this aspect, the solvent can be removed in a closed system that initially contains a partial pressure of the solvent in the system. The solvent can also be removed in a closed system that initially contains no partial pressure of the solvent in the system or the solvent can be removed in an open system.

In various aspects, removing the solvent involves heating the reservoir layer composition to a temperature above ambient temperature. In this aspect, the solvent can be removed in a closed system that initially contains a partial pressure of the solvent in the system. The solvent can be removed in a closed system that initially contains no partial pressure of the solvent in the system or the solvent can be removed in an open system.

DETAILED DESCRIPTION

The present invention provides methods for modulating and controlling the release rate of a bioactive agent from a polymer-bioactive agent coating on an implantable medical device by manipulating the surface population of polymer and bioactive agent in the device coating. The methods involve the judicious selection of polar and non-polar solvents, hydrophobic and hydrophilic polymers and bioactive agents as well as controlling the removal of the solvent by temperature and solvent partial pressure manipulations.

As used herein, "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, PFO closure devices, arterial closure devices, artificial heart valves and cerebrospinal fluid shunts.

As used herein, "device body" refers to a fully formed implantable medical device with an outer surface to which no coating or layer of material different from that of which the device itself is manufactured has been applied. "Outer surface" means any surface, however spatially oriented, that is in contact with bodily tissue or fluids. An example of a "device body" is a BMS, i.e., a bare metal stent, which is a fully-formed usable stent that has not been coated with a layer of any material different from the metal of which it is made. It is to be understood that device body refers not only to BMSs but also to any uncoated device regardless of what it is made.

Examples of device body materials useful with the present invention include, but are not limited to, stainless steel, 316L, nitinol, tantalum, tantalum alloy, titanium, titanium alloy, cobalt chromium, L-605, Haynes 25, MP35N, nickel-titanium-platinum alloy, niobium, niobium alloy, zirconium and zirconium alloy.

As used herein, a material that is described as a layer "disposed over" an indicated substrate, e.g., a device body, refers to a relatively thin coating of the material applied directly to essentially the entire exposed surface of the indicated substrate. The term "disposed over" may, however, also refer to the application of the thin layer of material to an intervening layer that has been applied to the substrate, wherein the material is applied in such a manner that, were the intervening layer not present, the material would cover substantially the entire exposed surface of the substrate.

As used herein, "hydrophilic" refers to a molecule that has an affinity for water. Almost all hydrophilic molecules are soluble in water. As used herein, the terms "polar" and 'hydrophilic" are used interchangeably.

As used herein, "hydrophobic" refers to a molecule that repels water. Hydrophobic molecules are generally insoluble in water. As used herein, the terms "non-polar" and "hydrophobic" are used interchangeably.

As used herein, "polar" refers to a molecule that has elements with different electronegativities at the termini of the bond between the elements resulting in a charge separation wherein the more electronegative element bears a partial negative charge and the less electronegative element bears a partial positive charge.

As used herein, "non-polar" refers to a molecule in which there are no elements bonded to one another that give rise to a charge separation or if there is a charge separation between the elements due to differing electronegativities, it is canceled out by an opposing charge separation. An example of the latter is carbon dioxide.

The bioactive agent, also referred to herein as a drug or a therapeutic agent, can be hydrophilic or hydrophobic and can be selected from a group that includes an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cytoprotective agent, a cardioprotective agent, a proliferative agent, an ABC A1 agonist or an antioxidant. A preferred bioactive agent is everolimus.

The release rate of a bioactive agent from a device coating depends strongly on the micro-phase morphology and molecular conformation of the bioactive agent and polymer in the coating. For example, when the concentration of polymer at the surface of a coating is higher than the concentration of bioactive agent, a relatively slow-release coating is obtained. This is mainly due to the fact that bioactive agent must work its way through the polymer in order to be released from the coating into the environment. Therefore, depending on the extent and type of polymer structure present in the outer layer of the coating, the path may be more or less tortuous.

In contrast, when the concentration of bioactive agent is higher at the surface of the coating than the polymer concentration, a relatively fast-release coating is obtained.

The present invention involves providing a device body, disposing a composition that includes a bioactive agent, a hydrophobic polymer that, if the bioactive agent is also hydrophobic, is more hydrophobic than the bioactive agent and a first hydrophobic solvent over the device body and removing the solvent from the composition to form a reservoir layer. Disposing the reservoir layer composition over the device body and removing the solvent from the composition are repeated until a desired reservoir layer thickness and bioactive agent concentration is achieved, then a release rate curve for the bioactive agent from the reservoir layer is determined. The release rate curve will provide a relative rate of release while manipulating coating variables, e.g., polymer hydrophobicity, will provide either faster or slower relative release rates. Thus, it is to be understood that the terms slow release and fast release are relative terms and are measured against each other. In addition, their values will be determinable and apparent to those skilled in the art from the disclosures herein.

A slow release coating can be obtained by concentrating polymer at the surface of a device coating, which can occur via manipulating the numerous variables described herein. It is to be understood that in each aspect of the invention a device body will be provided, a composition will be disposed over the device body, solvent will be removed and the steps repeated until a desired thickness and bioactive agent concentration is achieved. Release rate curves will then be obtained. For example, a drug-coated device can be immersed in an aqueous solution that contains organic solvent or surfactant. The release rate can then be determined by measuring the concentration of drug released into the solution at different time points. It is to be understood that other methods of obtaining release rates for a coating will be apparent to those skilled in the art and are encompassed by the present invention.

A first means of providing a slow release coating involves the use of a polymer that is more hydrophobic than a chosen bioactive agent and the use of a first hydrophobic solvent in the coating composition. Because of the hydrophobic nature of the polymer, it will preferentially localize with the hydrophobic solvent at the surface of the coating composition. In addition, the hydrophobic nature of the polymer will cause it to localize at the surface of a coating since thermodynamically, low surface tension is preferred. Thus, as the hydrophobic solvent evaporates, the hydrophobic polymer will remain at the surface, thereby providing a slow-release coating. It is to be understood that there will be both polymer and bioactive agent at the surface of the coating composition prior to and after drying, but the relative amounts can be controlled by the judicious selection of polymer, bioactive agent and solvent.

If an even slower release coating is desired a second hydrophobic solvent that is more hydrophobic than the first hydrophobic solvent can be substituted. This will cause even more of the hydrophobic polymer to migrate to the surface of the coating and form an even denser polymer network, and in turn a slower release coating.

For example, a coating composition can be made by using acetone as the solvent, everolimus as the bioactive agent and either poly(vinylidene fluoride-co-hexafluoropropylene) (PVDF-HFP) or poly(butyl methacrylate) (PBMA) as the polymer. In this case, PVDF-HFP and PBMA are both more hydrophobic than everolimus. Thus, the polymer will preferentially migrate to the surface of the coating composition and after solvent removal will form a slow release coating. Methods of coating a medical device with a coating composition are known to those skilled in the art.

If however, a slower release coating is desired, tetrahydrofuran (THF) can be used as the solvent. Since THF is more hydrophobic than acetone, even more of the hydrophobic polymer will migrate to the surface of the coating composition, and after solvent removal an even slower release coating will be formed. The use of a minimally polar solvent, or more hydrophobic solvent, in a coating composition can favor the formation of α-phase molecular conformations of the bioactive agent-polymer coating. Since α-phase molecular conformations are relatively compact, bioactive agent will take longer to work its way through the polymer at the surface of the coating to be released into the environment, thereby showing a slow-release rate.

Another property of THF that may add to this effect is its boiling point as compared to acetone. The boiling point for THF is approximately 66° C. and the boiling point for acetone is approximately 56° C. As will be described more fully below, the presence of a higher boiling point solvent in a coating composition can provide a slower release coating after solvent removal. Thus, the use of THF instead of acetone in a coating composition will provide a slower release coating, likely due to both its more hydrophobic nature and higher boiling point than acetone.

The formation of relatively fast release coatings follows the same strategy. For example, a coating composition containing N,N-dimethylformamide (DMF) as the solvent, everolimus as the bioactive agent and PBMA as the polymer can be used. In this situation, everolimus is more hydrophilic than PBMA and since DMF is relatively polar, everolimus will preferentially locate at the surface of the coating composition with DMF, thereby forming a relatively fast release coating upon solvent evaporation.

If however, an even faster release coating is desired, N,N-dimethylacetamide (DMAc) which is a more hydrophilic solvent than DMF, can be used. In this case, more everolimus will preferentially locate at the surface of the coating composition and upon solvent evaporation an even faster release coating will be formed.

The use of a relatively polar solvent in a coating composition can favor the formation of β-phase and γ-phase molecular conformations in the bioactive agent-polymer coating. β-phase and γ-phase conformations are relatively open structures, so bioactive agent is able to diffuse through the polymer relatively easily.

It is to be understood that taking into account hydrophobicity and polarity characteristics, different polymers, solvents and bioactive agents can be judiciously chosen to obtain a particular release rate profile. Indeed, mixtures of one or more polymers, solvents and bioactive agents can be used depending on the desired release rate profile. Methods of tailoring release rates by the judicious selection of polymers, solvents and bioactive agents will not require any undue experimentation and will be apparent to those skilled in the art using the disclosures herein.

Studies have shown that the quick evaporation of solvent, such as a 70:30 acetone/cyclohexanone mixture, from a coating composition provides faster stent drug release profiles than when a solvent is slowly removed during drying. When the solvent removal is slower, the hydrophobic polymer has more time to be enriched on the surface, thereby resulting in slower drug release.

Similar phenomena have been observed in a drug/PBMA system. PBMA is an amorphous polymer with a Tg, i.e., glass transition temperature, around room temperature. Drug release from such a coating is slower when the coating formulation initially contains a solvent with a higher boiling temperature.

Therefore, in addition to the selection of solvents based on polarity, the selection of solvents based on boiling points is also provided for by the present invention and will allow for another means of producing coatings with either slower or faster release rates.

For example, a coating composition that includes poly (lactic acid) (PLA) and a chloroform and 1,1,2-tri-chloroethane solvent mixture provides a faster release rate upon evaporation than a composition that includes PLA and methyl ethyl ketone (MEK) when both systems are dried to the point where <2 μg of residual solvent is left. The boiling point of MEK is approximately 80° C. at 1 atmosphere of pressure while the boiling point of a mixture of chloroform and 1,1,2-tri-chloro-ethane is approximately 74° C. at 1 atmosphere of pressure. The reason for the disparate release rates likely has to do with the amount of time that polymer has to form a tight polymer network while the solvent is evaporating from the coating composition. If the solvent evaporates quickly, then the polymer is not able to concentrate at the coating surface to form a very tight network, so the subsequent release rate will be relatively fast. In contrast, if the solvent has a higher boiling point, it will evaporate more slowly thereby allowing the polymer time to form a tighter network, which in turn will form a slower release coating upon solvent evaporation.

Polymers can also be non-crystalline and have blocks of different architecture with commensurate thermal and H-bonding properties. In these cases, it is the formation of phase domains, such as hydrogen bonding in the case of silk-elastin copolymers, instead of actual crystal formation that excludes drug.

In addition to the boiling points of the solvents affecting the rate of evaporation, the temperature at which the solvents evaporate as well as the partial pressure of the solvents will affect the final coating properties.

For example, if a coating composition is allowed to evaporate at ambient temperature or below, the polymer will have more time to form a tight network and the subsequent release rate will be relatively slow. As used herein, "ambient" temperature refers to room temperature and is approximately 20-25° C.

In contrast, if the coating composition is heated to a temperature above ambient temperature, the solvent will be removed more quickly and the polymer will not have as much time to form a tight network, thus a fast release coating will be formed.

Also of import to the evaporation rate of a solvent is whether evaporation proceeds in a closed system or an open system. If it occurs in a closed system then the partial pressure of the solvent in the closed environment will affect the evaporation rate and in turn the concentration of polymer at the surface of the coating.

In one aspect of the invention, the solvent is removed from a coating composition containing PVDF-HFP in a closed environment with a partial pressure of solvent in the environment, thereby increasing the amount of time for solvent removal, in turn forming a slow release coating. This may occur at ambient temperature or with heating, the former providing an even slower release coating. With judicious selection of heating temperatures, however, the subsequent release rate can further be controlled, thereby adding another means for tuning the release rate of a coating. Suitable solvent partial pressures and heating temperatures will be apparent to those skilled in the art, without undue experimentation, from the disclosures herein.

In another aspect, the solvent is removed from the coating composition in a closed environment with no partial pressure of solvent present in the environment. This will allow a slightly faster removal of solvent from the coating composition and in turn a slightly faster release rate than when a partial pressure of solvent is initially present. This effect may occur at ambient temperature or while heating, the former causing a slightly slower release rate, the latter a range of faster release rates, as described above.

In another aspect, the solvent is removed from the coating composition in an open system. In this aspect, solvent removal can occur at ambient temperature or with heating. In either case, the solvent will be removed faster than if removed in a closed system thereby providing another means of controlling the release rate of a subsequent coating.

In addition to modulating a stent surface so as to be relatively richer in either polymer or drug, there is also a pore size effect seen with polymers that have a Tg higher than ambient temperature, e.g., PLA. In this situation, solvents with higher boiling points will result in smaller pore sizes since phase inversion occurs at a lower rate.

The present invention provides a means for modulating the drug release from a polymer-drug composition, specifically a drug eluting stent (DES) coating, by manipulating the surface population of the polymer and drug.

Controlling drying time, temperature and the local environment around a stent coated with a coating composition of the invention all affect the respective amounts of polymer and drug on the surface of a stent coating. In addition, the selection of a solvent with a desirable boiling point, showing minimum solvent-polymer polar interactions can be used to manipulate surface tension and therefore the drug release mechanism.

The methods of the present invention are applicable to a range of drug delivery systems, preferably an everolimus in PVDF-HFP stent coating, an everolimus in PBMA stent coating and an everolimus in an ethylene vinyl alcohol (EVAL) stent coating, but are also applicable to bioabsorbable and durable polymeric materials, nanoparticle drug delivery systems and site-specific drug delivery systems.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention.

What is claimed is:

1. A method comprising the steps of:
    a. providing a device body;
    b. disposing a reservoir layer composition comprising a bioactive agent, a hydrophobic polymer that, if the bioactive agent is also hydrophobic, is more hydrophobic than the bioactive agent, and a first hydrophobic solvent over the device body;
    c. removing the first hydrophobic solvent from the composition to form a reservoir layer;
    d. repeating steps b. and c. until a desired reservoir layer thickness and bioactive agent concentration is achieved;
    e. determining a release rate curve for the bioactive agent from the reservoir layer; and
    f. selecting a desired release rate, the desired release rate being either slower or faster than the release rate determined in step e.;
    and
    on at least one subsequent occasion, executing steps a. to e. subject to one or more modifications based on the selection of step f.;
    wherein if the desired release rate selected is slower, at least one of the one or more modifications is selected from the group consisting of:
        substituting a second hydrophobic solvent for the first hydrophobic solvent, the second hydrophobic solvent being more hydrophobic than the first hydrophobic solvent;
        lowering the temperature of the environment during the solvent removal;
        if the solvent was removed in an open system during the previous execution of steps a. to e., removing the solvent in a closed system; and
        if the solvent was removed in a closed system during the previous execution of steps a. to e., increasing the initial partial pressure of the solvent in the system, the solvent being the first hydrophobic solvent if no substitution has been made, and the solvent being the second hydrophobic solvent if substitution has been made;
    and
    wherein if the desired release rate selected is faster, at least one of the one or more modifications is selected from the group consisting of:
        substituting a second hydrophobic solvent for the first hydrophobic solvent, the second hydrophobic solvent being less hydrophobic than the first hydrophobic solvent;
        increasing the temperature of the environment during the solvent removal;
        if the solvent was removed in a closed system during the previous execution of steps a. to e., decreasing the initial partial pressure of the solvent in the system, the solvent being the first hydrophobic solvent if no substitution has been made, and the solvent being the second hydrophobic solvent if substitution has been made; and
        if the solvent was removed in a closed system during the previous execution of steps a. to e., removing the solvent in an open system.

2. The method of claim 1, wherein the desired release rate selected is slower, and wherein at least one modification is the substitution of a second hydrophobic solvent that is more hydrophobic than the first hydrophobic solvent for the first hydrophobic solvent in the subsequent execution of steps a. to e.

3. The method of claim 1, wherein the desired release rate selected is faster, and wherein at least one modification is the substitution of a second hydrophobic solvent that is less hydrophobic than the first hydrophobic solvent for the first hydrophobic solvent in the repetition of steps a. to e.

4. The method of claim 1, wherein the desired release rate selected is slower, and at least one modification is lowering the temperature of the environment during the solvent removal.

5. The method of claim 1, wherein the desired release rate selected is slower, and the solvent was removed in an open system during the previous execution of steps a. to e., and wherein at least one modification is removing the solvent in a closed system.

6. The method of claim 1, wherein the desired release rate selected is slower, and the solvent was removed in a closed system during the previous execution of steps a. to e., and wherein at least one modification is increasing the initial partial pressure of the solvent in the system.

7. The method of claim 1, wherein the desired release rate selected is faster, and wherein at least one modification is increasing the temperature of the environment during the solvent removal.

8. The method of claim 1, wherein the desired release rate selected is faster, and the solvent was removed in a closed system during the previous execution of steps a. to e., and wherein at least one modification is decreasing the initial partial pressure of the solvent in the system.

9. The method of claim 1, wherein the desired release rate selected is faster, and the solvent was removed in a closed system during the previous execution of steps a. to e., and wherein at least one modification is removing the solvent in an open system.

* * * * *

UNITED STATES PATENT AND TRADEMARK OFFICE
CERTIFICATE OF CORRECTION

| | | |
|---|---|---|
| PATENT NO. | : 8,293,318 B1 | Page 1 of 1 |
| APPLICATION NO. | : 11/847222 | |
| DATED | : October 23, 2012 | |
| INVENTOR(S) | : Hsu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1406 days.

Signed and Sealed this
Thirtieth Day of September, 2014

Michelle K. Lee
*Deputy Director of the United States Patent and Trademark Office*